United States Patent [19]

Batorewicz

[11] 4,067,931
[45] Jan. 10, 1978

[54] FLAME RETARDANT POLYOXYMETHYLENE DIPHOSPHONATES

[75] Inventor: Wadim Batorewicz, New Haven, Conn.

[73] Assignee: Uniroyal, Inc., New York, N.Y.

[21] Appl. No.: 687,714

[22] Filed: May 19, 1976

[51] Int. Cl.$^2$ .............................................. C07F 9/02
[52] U.S. Cl. ........................... 260/927 R; 260/2.5 AJ; 260/45.7 P; 260/45.8 R; 260/932; 260/969
[58] Field of Search .................... 260/45.7 P, 2.5 AJ, 260/927 R, 932, 45.8 R, 969

[56] References Cited

U.S. PATENT DOCUMENTS 3,515,776 6/1970 Baranauckas et al. ...... 260/45.7 P X
3,737,397 6/1973 Baranauckas et al. ...... 260/45.7 P X
3,830,890 8/1974 Kerst et al. .................. 260/45.7 P X Primary Examiner—Lewis T. Jacobs
Attorney, Agent, or Firm—Anthony Lagani

[57] ABSTRACT

Polyoxymethylene diphosphonates having the formula

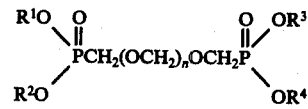

wherein the R groups are the same or different and are selected from alkyl, haloalkyl, hydroxyalkyl, or (R$^1$ and R$^2$) or (R$^3$ and R$^4$) are joined together to form a ring structure are disclosed. These compounds are useful as flame retardants for organic resins in general, and especially for foamed polyurethane resins.

12 Claims, No Drawings

FLAME RETARDANT POLYOXYMETHYLENE DIPHOSPHONATES

This invention relates to novel polyoxymethylene diphosphonates prepared from trialkyl phosphites and paraformaldehyde. These esters, which are useful as flame retardants especially for polyurethane foams, have the formula:

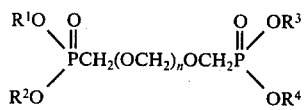

wherein the R groups are the same or different hydrocarbyl radicals and are selected from alkyl, haloalkyl, or hydrooxyalkyl, or $R^1$ and $R^2$ or $R^3$ and $R^4$ are joined together to form ring structures optionally substituted with up to two alkyl or haloalkyl groups, and $n$ is an integer from about 1 to 5.

Trialkyl phosphites are known to react with aliphatic aldehydes at low temperatures to give 1,4,2-dioxaphospholanes (Ramirez et al., J. Amer. Chem., Soc., 86, p. 514 (1964)) according to the reaction

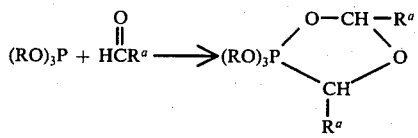

wherein $R^a$ is a lower akyl radical.

At elevated temperatures the reaction leads to an alkoxy translocation giving rise to acetal phosphonate esters of the structure:

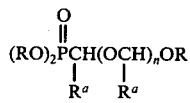

Aromatic aldehydes having electron withdrawing substituents in the para- or ortho-position are known to react with trialkyl phosphites to give 1,3,2-dioxaphospholanes (Ramirez et al., Tetrahedron, 23, page 2067, (1967)) of the structure:

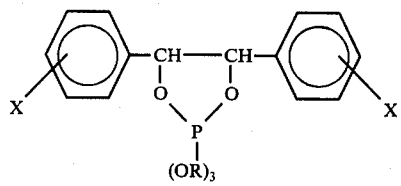

wherein X is such as $NO_2$. These compounds decompose to give epoxides and phosphate esters.

Neither of the above however discloses or suggests that paraformaldehyde reacts differently with trialkyl phosphites to give products which are different from those obtained with other aldehydes.

It is an object of this invention to produce new phosphonate esters. It is a further object of this invention to present a process for preparing such phosphonate esters. It is another object of this invention to prepare flame resistant polymers with the use of said phosphonate esters, and it is still another object of this invention to prepare flame retardant polymers, especially polyurethane foams, with the inclusion therein of the phosphonate esters.

The phosphonate esters of this invention are prepared from trialkyl phosphites and paraformaldehyde according to the reaction

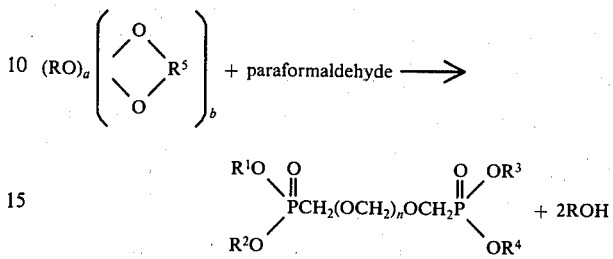

wherein R is alkyl or haloalkyl, $R^5$ is alkylene, or alkyl or haloalkyl substituted alkylene, $R^1$, $R^2$, $R^3$ and $R^4$ have the meanings of R or are hydroxyalkyl, or $R^1$ and $R^2$, and $R^3$ and $R^4$ respectively are combined to a group having the meanings of $R^5$, "$a$" has a value of 1 or 3, "$b$" correspondingly has a value of 1 or 0, and $n$ is an integer from 1 to about 5.

Preferably R is a radical selected from alkyl having 1 to 6 carbon atoms, or haloalkyl having 2 to 6 carbon atoms the halogens being bromine or chlorine, $R^5$ is alkylene having 2 to 3 carbon atoms optionally being substituted with up to two groups selected from alkyl and haloalkyl having 1 to 3 carbon atoms the halogen being bromine or chlorine, and $n$ is an integer from 1 to 3. Besides having the meanings of R and $R^5$, the radicals $R^1$, $R^2$, $R^3$ and $R^4$ may be hydroxyalkyl, due to the opening of the ring structures as discussed below, such as 2-hydroxyethyl, 2-dhydroxypropyl, 1-methyl-2-hydroxypropyl, 1-propyl-2-hydroxypropyl and others.

Numerous trialkyl phosphites can be employed in the preparation of the novel compositions of matter of this invention particularly those wherein R is methyl, ethyl, propyl, isopropyl, n-butyl, isobutyl, sec-butyl, tert-butyl, pentyl, hexyl, 2-chloroethyl, 2-bromoethyl, 3-chloropropyl, 3-bromopropyl, 3-chlorobutyl, 5-chloropentyl, 6-chlorohexyl, 2-hydroxyethyl, 3-hydroxypropyl; and $R^5$ is ethylene, propylene, isopropylene, 1,2-dimethylethylene, 1,3-dimethylpropylene, 1-(chloromethyl)ethylene, 1-(2-chloroethyl)ethylene, 1-methylpropylene, 1,2-(dichloromethyl)propylene, 1,3-(dichloromethyl)propylene, 1-(2-chloroethyl)propylene 1,3-di(2-chloroethyl)propylene, 1-(3-chloropropyl)propylene, 2-(3-chloropropyl)propylene and 1,3-di(3-dichloropropyl)propylene. The lower trialkyl phosphites, trimethyl and triethyl phosphite, are not as useful as the higher homologs for the present invention because they produce substantial amounts of dialkyl hydroxymethylphosphonate:

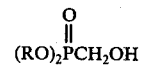

wherein R is $CH_3$, $CH_3CH_2$.

The formation of this by-product is probably the result of poor hydrolylic stability of the lower phosphites. Higher phosphites, such as tributyl phosphite, are readily converted to the desired diphosphonates without a solvent or in a moderately polar solvent such as acetonitrile.

Surprisingly, phosphites containing halogen substituents on the alkyl radical react very slowly with paraformaldehyde when heated together without a solvent or in a moderately polar solvent such as chloroform or acetonitrile. Such phosphites include, tris(2-chloroethyl) phosphite, tris(chloroisopropyl) phosphite, tris(3-chloropropyl)phosphite, tris(dichloroisopropyl) phosphite, tris(2,3-dibromopropyl) phosphite and the like. The reaction of paraformaldehyde with such phosphites, however, proceeds very smoothly in strongly polar solvents.

Cyclic phosphites such as substituted or unsubstituted 2-alkoxy-1,3,2-dioxaphospholanes and 2-alkoxy-1,3,2-dioxaphosphorinanes also require strong polar solvents to react with paraformaldehyde. Such phosphites are usually reacted with paraformaldehyde in dimethylformamide, although other appropriate solvents such as those disclosed below are also suitable. Whereas the 2-alkoxy-1,3,2-dioxaphosphorinanes react to give primarily symmetric polyoxymethylene diphosphonates having ($R^1$ and $R^2$) as well as ($R^3$ and $R^4$) ring structures as previously defined, the 2-alkoxy-1,3,2-dioxaphospholanes give a mixture of products as explained below.

It was discovered that the polyoxymethylene diphosphonates prepared from phosphites containing the five-membered 1,3,2-dioxaphospholane groupings contain hydroxyl groups. This apparently is a result of the susceptibility of the 1,3,2-dioxaphospholanes to nucleophilic attack which normally culminates in an acyclic product as a result of the ring cleavage. As shown in the Scheme below, the reaction of paraformaldehyde with phosphites containing the 1,3,2-dioxaphospholane grouping should result in a mixture of products. Although such a mixture is difficult to characterize, it appears to consist primarily of acyclic products.

SCHEME

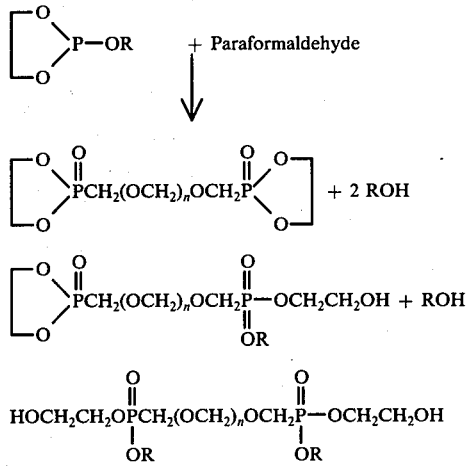

The compounds of this invention are prepared by the reaction of the phosphite with paraformaldehyde either without a solvent or in a non-protic solvent at temperatures of from about 50° to 150° C, preferably about 70° to 100° C.

The solvents useful in the present process include such as formamide, dimethylformamide, dimethylacetamide, hexamethylphosphoramide, dimethylsulfoxide, sulfolane and the like. The preferred solvent for the reaction leading to the polyoxymethylene diphosphonates of this invention is dimethylformamide. Protic solvents, such as alcohols cannot be employed in this transformation since under these conditions the reaction takes a different course, giving instead the known hydroxymethylphosphonates as major products.

Acid type catalysts may optionally be employed in the process. These include concentrated sulfuric acid, p-toluenesulfonic acid, oxalic acid, boron trifluoride, and the like. These catalysts do not substantially increase the rate of the reaction, however.

The reaction of trialkyl phosphites with paraformaldehyde is conveniently carried out by the stepwise addition of parafomaldehyde, preferably in a fine powder form, to the phosphite. Usually the phosphite is dissolved in an appropriate polar solvent. The resulting suspension is heated with stirring. The heating may conveniently be done using a steam bath, for example. Initially the course of the reaction can be followed by observing the disappearance of the suspension of paraformaldehyde. The stepwise addition of paraformaldehyde is continued until all the phosphite has been converted to the phosphonate. The excess paraformaldehyde may be separated by filtration, with the filtrate then being subjected to vacuum distillation to remove solvent and by-products. The product is usually recovered as the distillation residue.

Since bromine readily reacts with a phosphite, the end of the reaction can be determined by treating an aliquot of the reaction mixture with a solution of bromine in chloroform, for example. The course of this reaction can also be conveniently followed by infrared (IR) spectroscopy by observing the gradual disappearance of the absorption bands in the 700–750 cm$^{-1}$ region associated with the phosphite P-O-R structure and the appearance of a band in the 1210–1230 cm$^{-1}$ region associated with the P=O structure.

The polyoxymethylene diphosphonates of this invention find utility as flame retardants for organic resins. Particularly for polyurethanes, polyesters, polystyrenes and polyvinyl chloride. They are especially useful as flame retardants in both flexible and rigid polyurethane foams. These novel compositions of matter have molecular weights generally greater than about 500 and thus have very low volatility which is a desirable feature as this property renders them substantially non-fugitive, thereby providing long lasting protection to the polymer. In addition, certain compositions of this invention contain hydroxyl groups so that they can be effectively employed with polyether polyols normally used in polyurethane production as reactive flame retardants to provide essentially permanent flame retardancy to be polyurethanes.

Liquid technology is employed in the production of foamed polyurethanes. Because the preferred compositions of the invention are fluid oils at room temperature and have very good solubility in the polyether polyols normally employed in polyurethane foam manufacture, they are eminently suited for that application.

EXAMPLE I

Reaction of Paraformaldehyde with tris(1-chloro-2-propyl) Phosphite

A solution of the phosphite (324 g, 1 mole) in dimethyl formamide (600 ml) was heated with stirring on a steam bath to about 80°–90° C. Paraformaldehyde powder was added incrementally to this solution. After each addition, the mixture was stirred and heated until paraformaldehyde reacted, as indicated by the disappearance of the white suspension. The consumption of paraformaldehyde was rapid at the beginning but became progressively slower toward the end of the conversion. The reaction was stopped when an aliquot of the reaction mixture did not discolor bromine-chloroform solution, indicating complete conversion of the phosphite. It required about 60 g of paraformaldehyde. The mixture was allowed to cool to room temperature and was filtered to remove small amounts of unreacted paraformaldehyde which remained in suspension. The filtrate was concentrated under reduced pressure (0.3–0.5 mm Hg) at about 100° C pot temperature to remove the solvent and the by-products. The product, a tan clear oil, was recovered as the distillation residue.

The product analysis was 10.1% P and 26.9% Cl which corresponds to a value of "$n$" being an average of 2.

EXAMPLE II

Reaction of Paraformaldehyde with tris(1-bromo-2-propyl) Phosphite

The procedure of Example I is repeated except that tris (1-bromo-2-propyl) phosphite (457 g, 1 mole) is used. It requires about 60 g of paraformaldehyde. The product is a tan clear oil.

EXAMPLE III

Reaction of Paraformaldehyde with tris(2-chloroethyl) Phosphite

The procedure of Example I as repeated with the different phosphite and utilizing an oxalic acid catalyst. The ingredients used were:

| Phosphite | 314g | 1.17 mole |
|---|---|---|
| Oxalic acid | 2g | |
| Dimethyl formamide | 500ml | |

It required about 70g of paraformaldehyde to effect the transformation. The product was a tan clear oil.

Analysis: 12.4% P, 26.9% Cl

The average value of "$n$" was 2 which corresponds to a theoretical P content of 12.1% and a theoretical Cl content of 27.4%.

EXAMPLE IV

Reaction of Paraformaldehyde with tris-(1,3-dichloro-2-propyl) Phosphite 100.6 g (0.24 mole) of the phosphite was placed in 100 ml dimethyl formamide as in Example I. The procedure of Example I was then repeated. It took about 18g of paraformaldehyde to effect the transformation. The product was a very waxy crystalline solid.

Analysis: 8.54% P, 40.1% Cl

The average value of "$n$" was 2.

EXAMPLE V

Tributyl phosphite (43.4 g, 0.173 mole) was treated with paraformaldehyde powder (about 9g) as described in Example I except that no solvent was employed. The product was a tan oil.

Analysis: 12.5% P.

The average value of "$n$" was 2.

EXAMPLE VI

Reaction of Paraformaldehyde with 1,4-bis(1',3',2'-dioxapholane)-1,4-dioxabutane 1. Preparation of the Phosphite The phosphite was prepared by a transesterification of trimethyl phosphite (620 g, 5.0 mole) with ethylene glycol (465 g, 7.5 moles) at about 100° C. A vigorous evolution of methanol was observed during this reaction. When the evolution of the by-product methanol ceased, reduced pressure (10–20mm of Hg) was applied to remove any residual methanol. On cooling the product crystallized as white needles. The phosphite was used in the next step without purification.

2. The Conversion of the Phosphite to the Phosphonate

The phosphite was dissolved in dimethyl formamide (1,300 ml) and treated with paraformaldehyde in a manner described in Example I. It required about 297 g of paraformaldehyde to effect the transformation. The product was a tan viscous oil. Infrared analysis showed the presence of hydroxyl groups, indicating that considerable ring cleavage had occurred.

Analysis: 15.2% P; OH No. 254.

EXAMPLE VII

Reaction of Paraformaldehyde with 2-(1'-chloro-2'-propoxy)-1,3,2-dioxaphospholane 1. Preparation of the Phosphite Ethylene glycol (62.0 g, 1.0 mole) was added dropwise with stirring to $PCl_3$ (137 g, 1.0 mole) dissolved in dichloroethane (250 ml). Occasional cooling as required to maintain the reaction temperature at about 5° to 10° C. When the addition of ethylene glycol was completed, the resulting solution was stirred at ambient temperature for about one hour, then concentrated under reduced pressure to remove any residual HCl and the solvent. The product was purified by distillation under reduced pressure, giving the phosphite as a clear liquid (b.p. 62°–66° C, at 1.5–2.0mm of Hg pressure).

2. Conversion of the Phosphite to the Phosphonate

| Phosphite | 46.5 g, | 0.24 mole |
|---|---|---|
| Dimethyl Formamide | 50 ml | |

The reaction was carried out as described in Example 1. It required about 16g of paraformaldehyde to effect the transformation. The product is a clear viscous oil. IR analysis showed the presence of OH groups, indicating that considerable ring cleavage occurred during the transformation.

Analysis: 12.6% P; 11.2% Cl.

EXAMPLE VIII

Reaction of Paraformaldehyde with 5,5-Dimethyl-2-methoxy-1,3,2-dioxaphosphorinane 1. Preparation of the Phosphite The phosphite was prepared by a transesterification of 2,2-dimethyl-1,3-propanediol (104 g, 1.0 mole) with trimethyl phosphite (150 g, 1.2 moles) at about 100° C. A vigorous evolution of methanol was observed during the reaction. When the evolution of the by-product methanol ceased, reduced pressure (10–20mm of Hg) was applied to remove residual methanol and unreacted trimethyl phosphite. The product was purified by distillation under reduced pressure. It is a clear liquid (b.p. 49°–52° C at 0.5 mm of Hg pressure).

2. Conversion of the Phosphite to the Phosphonate

| Phosphite | 28.4 g | 0.17 mole |
|---|---|---|
| Dimethyl Formamide | 35 ml | |

The reaction was carried out as described in Example I. It required about 9 g of paraformaldehyde to effect the transformation. The product was a tan viscous resin.

Analysis: 15.3% P.

EXAMPLE IX

This example illustrates the utility of the compounds of this invention as flame retardants in flexible polyurethane foam.

The flexible foams were prepared by a hand-mix technique using the conventional one-shot process. For this purpose, all the ingredients except the polyisocyanate are thoroughly mixed in a beaker and thereafter the polyisocyanate is added while rapidly agitating the mixture with an air-driven stirrer. The liquid contents of the beaker are then poured into a mold, where within a short period of time a foam develops. The foam is cured at 100° C for 20 min. then over night at room temperature. The flame resistance is determined by the Oxygen Index Text (A.S.T.M. D-2863).

The foam compositions and Oxygen Index results were as given in Table I.

Table I

| Experiment | A | B | C |
|---|---|---|---|
| Formulation parts by weight | | | |
| Polyol (1) | 200 | 200 | 200 |
| Surfactant (2) | 4 | 4 | 4 |
| Triethylenediamine | 0.6 | 0.6 | 0.6 |
| Amine catalyst (3) | 0.6 | 0.6 | 0.6 |
| Stannous octoate catalyst | 0.6 | 0.6 | 0.6 |
| Water | 8 | 8 | 8 |
| Polyisocyanate (4) | 96 | 96 | 96 |
| Diphosphonate of Example I | — | 32.9 | — |
| Diphosphonate of Example III | — | — | 32.9 |
| Results | | | |
| Oxygen Index | 16.8 | 21.6 | 21.6 |

Remarks:
(1) Propoxylated glycerol having molecular weight ca. 3000 and OH# ca. 50.
(2) Silicone compound, DC-190 of Dow Corning Corp.
(3) A-1 of Union Carbide Corp.
(4) 80/20 mixture of 2,4- and 2,6-isomers of toluene diisocyanate.

EXAMPLE XI

This example shows the utility of the compounds herein in a rigid polyurethane foam. The foams were prepared in accordance with the procedure of Example X (except for curing at 100° C) with the formulations and results being given in Table II.

Formulation D contains no flame retardant. Formulation E contains the diphosphonate of Example VI which is a reactive flame retardant due to the hydroxyl groups. Formulation F contains the diphosphonate of Example III which is an additive flame retardant.

Table II

| Experiment | D | E | F |
|---|---|---|---|
| Formulation parts by weight | | | |
| Polyol (1) | 70 | 51.6 | 70 |
| Polyol (2) | 30 | 22.1 | 30 |
| Surfactant (3) | 2 | 2 | 2 |
| Triethylenediamine (4) | 1 | 1 | 1 |
| Trichlorofluoromethane | 45 | 45 | 45 |
| Diphenylmethane Diisocyanate | 136 | 127 | 136 |
| Diphosphonate of Example VI | — | 26.3 | — |
| Diphosphonate of Example III | — | — | 31 |
| Results | | | |

Table II-continued

| Experiment | D | E | F |
|---|---|---|---|
| Oxygen Index | 20.6 | 23.7 | 23.5 |

Remarks:
(1) Amine initiated polyether polyol, molecular weight ca. 350, OH# ca. 520.
(2) Propoxylated sorbitol, molecular weight ca. 700, OH# ca. 480.
(3) Silicone compound, DC-193 of Dow Corning Corp.
(4) 30% in diethylene glycol solvent.

What is claimed is:

1. A polyoxymethylene diphosphonate of the formula $$\begin{array}{cc} R^1O \quad O & O \quad OR^3 \\ \diagdown \| & \| \diagup \\ PCH_2(OCH_2)_nOCH_2P \\ \diagup & \diagdown \\ R^2O & OR^4 \end{array}$$

wherein $R^1$, $R^2$, $R^3$ and $R^4$ are the same or different and are selected from the group consisting of alkyl having 1 to 6 carbon atoms, haloalkyl having 2 to 6 carbon atoms with the halogen being chlorine or bromine, hydroxyalkyl having 2 to 5 carbon atoms, $R^1$ and $R^2$, and $R^3$ and $R^4$ are respectively joined together to form ring structures having 2 to 3 carbon atoms said ring structures being optionally substituted with up to two methyl or chloromethyl groups, and wherein $n$ is an integer from 1 to 3.

2. The diphosphonate of claim 1, wherein $R^1$, $R^2$, $R^3$ and $R^4$ are the same and are chloroalkyl having 2 to 6 carbon atoms.

3. The diphosphonate of claim 1 wherein $R^1$, $R^2$, $R^3$ and $R^4$ are each 1-chloro-2-propyl groups.

4. The diphosphonate of claim 1 wherein $R^1$, $R^2$, $R^3$ and $R^4$ are the same and are 2-chloroethyl groups.

5. The diphosphonate of claim 1 wherein both $R^1$ and $R^2$ and $R^3$ and $R^4$ respectively are joined together to form ring structures with 2 carbon atoms said ring structures being optionally substituted with up to two methyl groups.

6. A process for preparing polyoxymethylene phosphonates comprising reacting paraformaldehyde at a temperature of from 50° to 150° C. with a phosphite having the formula $$(RO)_aP\left(\begin{array}{c} \diagup O \diagdown \\ \diagdown O \diagup R^5 \end{array}\right)_b$$

wherein R is selected from alkyl having 1 to 6 carbon atoms and haloalkyl having 2 to 6 carbon atoms with the halogen being chlorine or bromine, $R^5$ is alkylene having 2 to 3 carbon atoms optionally substituted with alkyl and haloalkyl groups having up to 3 carbon atoms with the halogen being chlorine or bromine, "a" has a value of 1 or 3, and "b" correspondingly has a value of 1 or 0.

7. The process of claim 6 wherein the R groups are alkyl having 3 to 6 carbon atoms.

8. The process of claim 6 wherein the reaction is carried out in a non-protic solvent.

9. The process of claim 8 wherein the solvent is diemthyl formamide.

10. The process of claim 6 wherein "a" is 3, "b" is O, R is haloalkyl having 2 to 6 carbon atoms with the halogen being chlorine or bromine, and the reaction occurs in the presence of a polar solvent.

11. The process of claim 10 wherein the solvent is dimethyl formamide.

12. The process of claim 6 wherein the temperature is from about 70° to 100° C.

* * * * *